United States Patent
Ryu et al.

(10) Patent No.: US 9,028,749 B2
(45) Date of Patent: May 12, 2015

(54) APPARATUS AND METHOD FOR DECONTAMINATING AND STERILIZING CHEMICAL AND BIOLOGICAL AGENT

(75) Inventors: Sam Gon Ryu, Daejeon (KR); Hae Wan Lee, Daejeon (KR)

(73) Assignee: Agency for Defense Development, Daejeon (KR)

( * ) Notice: Subject to any disclaimer, the term of this patent is extended or adjusted under 35 U.S.C. 154(b) by 228 days.

(21) Appl. No.: 13/698,348

(22) PCT Filed: Apr. 18, 2011

(86) PCT No.: PCT/KR2011/002740
§ 371 (c)(1),
(2), (4) Date: Jan. 7, 2013

(87) PCT Pub. No.: WO2011/149188
PCT Pub. Date: Dec. 1, 2011

(65) Prior Publication Data
US 2013/0136654 A1     May 30, 2013

(30) Foreign Application Priority Data
May 24, 2010 (KR) .................. 10-2010-0047817

(51) Int. Cl.
*A61L 2/00* (2006.01)
*A62B 7/08* (2006.01)
(Continued)

(52) U.S. Cl.
CPC ... *A61L 2/22* (2013.01); *A61L 2/14* (2013.01); *A61L 2/208* (2013.01); *A61L 9/03* (2013.01);
(Continued)

(58) Field of Classification Search
CPC .................. A61L 2/00; A61L 9/18

USPC ......... 422/22, 121, 123, 186.04, 186.05, 305, 422/906; 204/157.15, 164
See application file for complete search history.

(56) References Cited

U.S. PATENT DOCUMENTS

| | | |
|---|---|---|
| 4,643,876 A | 2/1987 | Jacobs et al. |
| 5,667,753 A | 9/1997 | Jacobs et al. |

FOREIGN PATENT DOCUMENTS

| | | |
|---|---|---|
| EP | 0456135 | 11/1991 |
| EP | 0774263 | 5/1997 |

(Continued)

OTHER PUBLICATIONS

Korean Intellectual Property Office English Translation of KR1008225990000.*

*Primary Examiner* — Monzer R Chorbaji
(74) *Attorney, Agent, or Firm* — Harness, Dickey & Pierce, P.L.C.

(57) ABSTRACT

Disclosed are apparatus and method for decontaminating and sterilizing chemical and biological agents, which can efficiently decontaminate and sterilize high precision electronic devices, communication devices, computers or inside of vehicles and air planes contaminated with chemical and biological agent by using mixture of non-thermal atmospheric pressure air plasma and oxidizing peroxide vapor. The apparatus according to the present invention comprises a decontamination and sterilization chamber 10; a first fluid supplying line L1 and a second fluid supplying line L2, which are installed in the form of closed circuit between the inlet 11 and outlet 12 of the decontamination and sterilization chamber 10; a peroxide vapor supplier which is installed on the first fluid supplying line; and a non-thermal atmospheric pressure air plasma reactor 70 which is installed on the second fluid supplying line L2.

24 Claims, 2 Drawing Sheets

(51) Int. Cl.
    *B01J 19/08*   (2006.01)
    *A61L 9/00*    (2006.01)
    *C07C 1/00*    (2006.01)
    *A61L 2/22*    (2006.01)
    *A61L 2/14*    (2006.01)
    *A61L 2/20*    (2006.01)
    *A61L 9/03*    (2006.01)
    *A61L 9/22*    (2006.01)
    *H05H 1/24*    (2006.01)

(52) U.S. Cl.
    CPC ............ *A61L 9/22* (2013.01); *A61L 2209/211*
    (2013.01); *H05H 1/2406* (2013.01); *H05H 2001/2412* (2013.01); *H05H 2001/2443* (2013.01)

(56) References Cited

FOREIGN PATENT DOCUMENTS

| EP | 1736175 | 12/2006 | | |
|---|---|---|---|---|
| KR | 10-0822599 | 4/2008 | | |
| KR | 1008225990000 | * 4/2008 | ................ | A61L 2/14 |
| WO | 03/090875 | 11/2003 | | |

* cited by examiner though decontamination and sterilization apparatus disclosed in the present invention is configured to decontaminate and sterilize high precision electronic devices, communication devices, computers or inside of vehicles and airplanes contaminated with chemical and biological agent by circulating the mixture of non-thermal atmospheric pressure air plasma and oxidizing peroxide vapor in the closed circuit, the decontamination and sterilization chamber may be constructed to be open to the atmosphere.

APPARATUS AND METHOD FOR DECONTAMINATING AND STERILIZING CHEMICAL AND BIOLOGICAL AGENT

TECHNICAL FIELD

The present invention relates to apparatus and method for decontaminating and sterilizing chemical and biological agents, which can efficiently decompose and remove toxic chemical and biological agents on the surface of a device or an object contaminated with chemical and biological agent in a short time by using mixture of non-thermal atmospheric pressure air plasma and oxidizing peroxide vapor.

BACKGROUND ART

In sterilizing and decontaminating toxic chemical and biological agents which are used for warfare or industrial purpose, strong base alkali aqueous solution is generally used, and liquid oxidant is also being developed. These decontamination/sterilization methods, however, can cause erosion of the surface treated and disorder of the device due to the use of strong corrosive liquid state decontamination agents, which is inappropriate for use in decontaminating high precision electronic devices, communication devices, computers or inside of vehicles and airplanes.

In order to overcome the problems of corrosive liquid state decontamination agent, new methods of sterilizing and decontaminating microorganism and chemical material used as chemical and biological agents, which use low temperature plasma, have been developed.

Korean Patent No. 0822599, for example, discloses a method of n decontamination in which plasma is generated by using inert gas or argon as a discharge medium. This method, however, has the problem of high cost due to the use of argon which is a high price inert gas, and the inconvenience of carrying high pressure gas container. Also, since the generated plasma free radicals diminish very rapidly in the air with short lifetime, the effect of decontamination greatly deteriorates on the objects of decontamination/sterilization which are far from the plasma exit hole, which is technically big limitation. In other words, above prior art methods are not appropriate for decontamination/sterilization of the objects or devices contaminated by chemical and biological agents which are in a chamber which is relatively large in space that plasma flame cannot directly touch the contaminated objects.

For another example, Korean Patent No. 0643594 discloses a decontamination/sterilization method through vaporizing oxidizing liquid such as hydrogen peroxide, but has the problem of excessive time especially for decontaminating chemical agent due to lack of prompt reactivity, and excessive consumption of hydrogen peroxide due to the adoption of a single fluid supply line.

DISCLOSURE OF INVENTION

Technical Problem

The present invention has been designed to solve the above mentioned problems of prior art methods of decontamination and aims to provide apparatus and method for decontaminating and sterilizing chemical and biological agents, which can efficiently decontaminate and sterilize high precision electronic devices, communication devices, computers or inside of vehicles and air planes contaminated with chemical and biological agent by simultaneously using non-thermal atmospheric pressure air plasma and oxidizing peroxide vapor.

Solution to Problem

In order to achieve the object of the present invention, one embodiment of the present invention comprises a decontamination and sterilization chamber which contains object to be decontaminated and sterilized, and decontaminates and sterilizes chemical and biological agent on the surface of the object;

a first fluid supplying line and a second fluid supplying line, which are installed in the form of closed circuit between the inlet and outlet of the decontamination and sterilization chamber so that fluid can be circulated; a peroxide vapor supplier which is installed on the first fluid supplying line to supply first fluid, which is oxidizing peroxide vapor, into the decontamination and sterilization chamber through the first fluid supplying line using air as carrier gas; and an non-thermal atmospheric pressure air plasma reactor which is installed on the second fluid supplying line and generates air plasma containing plasma free radical and active species by plasmarizing a portion of mixture of gases comprising peroxide vapor, water vapor and air exited through the exit of the decontamination/sterilization chamber so that the air plasma, as a second fluid, is supplied to the decontamination and sterilization chamber through the rear end of the peroxide vapor supplier.

The second fluid supplying line is preferably branched from the first fluid supplying line on the exit side of the decontamination/sterilization chamber, and installed connected to the rear end of the supplier.

Preferably, a nitrogen-containing base gas supply is installed inside the decontamination/sterilization chamber to supply nitrogen-containing base gas for controlling pH of the oxidizing peroxide vapor.

Preferably, the air mixture contains a small amount of nitrogen-containing base gas.

Preferably, the peroxide vapor supplier includes a peroxide aqueous solution supply that supplies oxidizing peroxide aqueous solution and a vaporizer which is connected to the peroxide aqueous solution supply in order to heat and evaporate the oxidizing peroxide aqueous solution.

Preferably, the nitrogen-containing base gas supply is connected to the fluid mixer installed between the peroxide vapor supplier and the decontamination/sterilization chamber, or directly connected to the decontamination/sterilization chamber.

Preferably, a fluid gauge is installed in the path between the peroxide aqueous solution supply and the vaporizer for controlling the amount of fluid of the oxidizing peroxide aqueous solution, and a fluid gauge is installed in the path between the nitrogen-containing base gas supply and the mixer for controlling the amount of fluid of the nitrogen-containing base gas.

Preferably, a dehumidifier is installed on the second fluid supplying line which controls the relative humidity inside the decontamination/sterilization chamber not higher than 40% by circulating a carrier gas only.

Preferably, a blower is installed on the front of the non-thermal atmospheric pressure air plasma reactor and on the front of the peroxide vapor supplier in order to blow air or air mixture.

Preferably, the non-thermal atmospheric pressure air plasma reactor includes two electrodes that cause dielectric barrier discharge, at least one of which is coated with dielectric material or filled with adsorbent or catalytic material between the electrodes.

Preferably, the non-thermal atmospheric pressure air plasma reactor comprises two flat-type electrodes.

Preferably, the non-thermal atmospheric pressure air plasma reactor comprises an external coaxial electrode and core-type internal electrode.

Preferably, the catalytic material filled between the two electrodes is one-body ceramic honeycomb coated with catalytic material, or one selected from the group consisting of bead, pallet or granule-type aggregates.

Preferably, the catalytic material is precious metals including Pt, Pd, Rh and Ru which is supported by metal oxide, transition metal oxide including CrOx and CuOx which is supported by metal oxide, molecular sieve including zeolite 13X, or semiconductor material including $TiO_2$, $ZrO_2$ and MgO.

Preferably, the chemical and biological agent includes one selected from the group consisting of organic phosphorus based compound that can be used for warfare chemical gas or agricultural agent, sulphur or nitrogen-containing compound, cyan based compound, chloride or fluoride-containing compound, and pathogenic bacteria, virus and toxins that can be used as a biological weapon.

Preferably, the peroxide is hydrogen peroxide.

Preferably, the nitrogen-containing base gas is ammonia.

Another embodiment of the present invention provides a method for decontaminating and sterilizing chemical and biological agents, which decontaminates and sterilizes object contaminated with chemical and biological agents by treating the contaminated object with a mixture of oxidizing peroxide vapor, nitrogen-containing base gas and plasma free radical/active species generated by passing through the non-thermal atmospheric pressure air plasma, using air as carrier gas.

Another embodiment of the present invention provides a method for decontaminating and sterilizing chemical and biological agents, which comprises: a stabilization step in which the object for decontamination/sterilization contaminated by chemical and biological agent is placed in the decontamination/sterilization chamber, the chamber is closed, and controlling relative humidity inside the decontamination/sterilization chamber not higher than 40% at room temperature by circulating air which is a carrier gas; a decontamination/sterilization step in which, after the stabilization step is completed, micro-condensation of peroxide vapor is generated on the surface of the object for decontamination/sterilization and inside the decontamination/sterilization chamber by evaporating peroxide aqueous solution and supplying and circulating the vapor inside the decontamination/sterilization chamber; and a post-processing step in which, after the decontamination/sterilization step is completed, a portion of the air mixture consisting of peroxide vapor, water vapor and air exited from the exit of the decontamination/sterilization chamber is plasmarized through the non-thermal atmospheric pressure air plasma reactor, then additional decontamination of the surface of the object and inside of the decontamination/sterilization chamber is carried out by using air plasma comprising plasma free radicals and active species and toxical material including peroxide remaining in the decontamination/sterilization chamber is decomposed into harmless material.

Preferably, the decontamination/sterilization step comprises the step of supplying, along with the peroxide vapor, plasma free radical and activity radical generated by simultaneously operating the non-thermal atmospheric pressure air plasma reactor to the decontamination/sterilization chamber.

Preferably, the decontamination/sterilization step comprises the step of controlling pH of the peroxide vapor supplied to the decontamination/sterilization chamber by supplying nitrogen-containing base gas to the decontamination/sterilization chamber.

Preferably, supply of peroxide vapor is stopped after micro-condensation has occurred at the decontamination/sterilization step, and only air, the carrier gas, is circulated.

Preferably, the peroxide vapor and the air mixture are controlled in the temperature range of 55-65° C. before the peroxide vapor and the air mixture are supplied to the decontamination/sterilization chamber.

Advantageous Effects of Invention

By using the method and apparatus of the present invention, which uses non-thermal atmospheric pressure air plasma and oxidation vapor of peroxide together, it is possible to decontaminating and sterilizing chemical and biological agent remaining on the high precision electronic devices, communication devices, computers or inside of vehicles and air planes in a rapid and efficient way, which is a great advance compared to the prior method using aqueous solution state decontamination agent and which can be more easily used for warfare and industrial purpose since decontamination/sterilization of chemical and biological agents deeply seated in the objects or devices of treatment is more easily carried out compared to conventional method using plasma due to the increased lifetime in the air and the use of oxidation vapor.

BEST MODE FOR CARRYING OUT THE INVENTION

The invention will be described in more detail with reference to the drawings.

The present invention provides hybrid-type apparatus and method for decontaminating and sterilizing chemical and biological agents, which can efficiently detoxicate and sterilize high precision electronic devices, communication devices, computers or inside of vehicles and air planes contaminated with chemical and biological agent by simultaneously using non-thermal atmospheric pressure air plasma and oxidizing peroxide vapor.

The hybrid-type decontamination/sterilization apparatus, as described below, is constructed as a closed circuit system, including dual fluid supplying line comprising a fluid supplying line which supplies oxidation gas evaporated by a vaporizer to the decontamination/sterilization chamber, and a fluid supplying line which supplies non-thermal atmospheric pressure air plasma passed by the non-thermal atmospheric pressure air plasma reactor into the decontamination/sterilization chamber.

Figure 1:
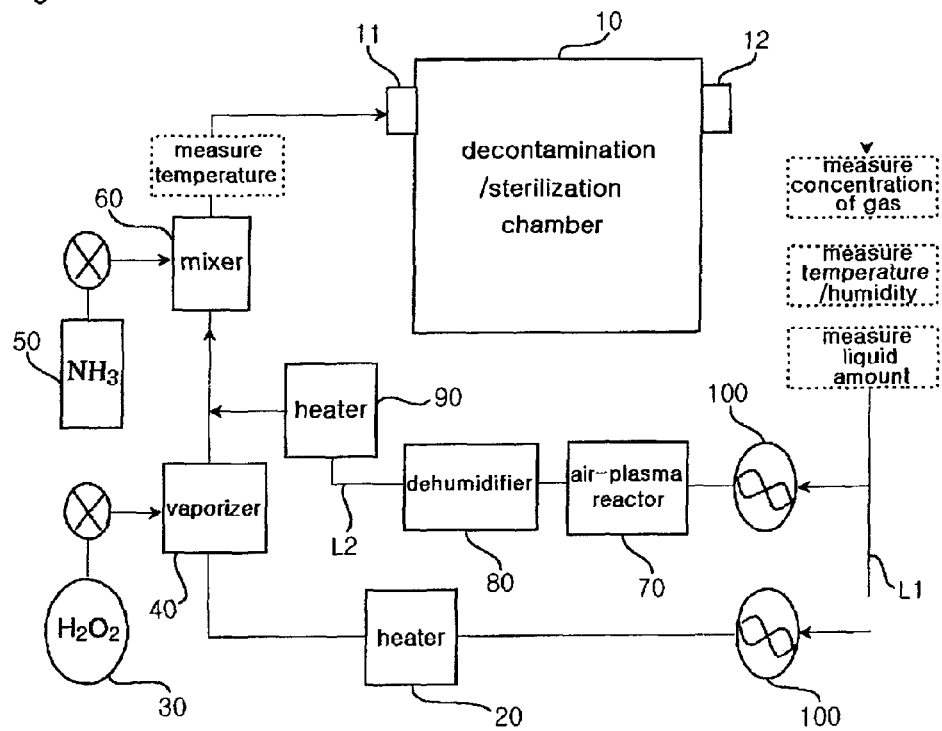
FIG. 1 schematically illustrates the structure of the chemical and biological agent decontamination/sterilization apparatus of the present invention.

More specifically, the apparatus for decontaminating and sterilizing chemical and biological agents according to the present invention, as shown in FIG. 1, comprises a decontamination and sterilization chamber 10 which contains object to be decontaminated and sterilized, and decontaminates and sterilizes chemical and biological agent on the surface of the object;

a first fluid supplying line L1 and a second fluid supplying line L2, which are installed in the form of closed circuit between the inlet 11 and outlet 12 of the decontamination and sterilization chamber 10 so that fluid can be circulated; a peroxide vapor supplier which is installed on the first fluid supplying line to supply first fluid, which is oxidizing peroxide vapor, into the decontamination and sterilization chamber 10 through the first fluid supplying line using air as carrier gas; and an non-thermal atmospheric pressure air plasma reactor 70 which is installed on the second fluid supplying line L2 and generates air plasma containing plasma free radical and activity radical by plasmarizing a portion of mixture of gases comprising peroxide vapor, water vapor and air exited through the exit 12 of the decontamination/sterilization chamber 10 so that the air plasma, as a second fluid, is supplied to the decontamination and sterilization chamber 10 through the rear end of the peroxide vapor supplier.

The decontamination and sterilization chamber 10 can be a closed chamber that can contain objects or devices that are contaminated with chemical and biological agents such as high-precision electronic devices, communication devices, computers, clothes, weapons or medical equipments, and the chamber 10 includes structures such as vehicles, airplanes, rooms or inside of a building, which can be closed and which contains objects or device, or the surfaces of the structure that need to be decontaminated and sterilized. The chemical and biological agents include organic phosphorous or nitrogen-containing compounds cyanide compounds, chloride or fluorine-containing compounds, which can be used as warfare chemical gases or agricultural chemicals, and pathogenic bacteria, virus or toxins, which can be used as biological weapons.

The oxidizing peroxide vapor, which is supplied to the decontamination/sterilization chamber 10, is in saturated state, and the oxidizing peroxide vapor is supplied into the chamber 10 as the carrier gas or the air, which fills the chamber 10 and two fluid supplying lines L1, L2 in advance, circulates when the oxidizing peroxide vapor is supplied to the decontamination/sterilization chamber 10.

The peroxide vapor supplier comprises a peroxide aqueous solution supply 30 which supplies oxidizing peroxide aqueous solution, and a vaporizer 40 which is connected to the peroxide aqueous solution supply 30 to heat and evaporate the oxidizing peroxide aqueous solution.

The first fluid supplying line L1 and the second fluid supplying line L2 are preferably installed connected as above so that the first and the second fluids are joined before they are supplied to the decontamination/sterilization chamber 10, or they can be installed separately.

Here, the second fluid supplying line L2 is configured so that the oxygen present in the air mixture passing the non-thermal atmospheric pressure air plasma reactor 70 and a small amount of peroxide or a portion of water (water vapor) are converted to free radical such as ozone ($O_3$), one-valence oxygen ($1O_2$), or activity radical such as hydroxyl radical, peroxy radical to be supplied into the chamber 10 during decontamination/sterilization process, and after decontamination/sterilization process is completed, post-processing step can be carried out by the non-thermal atmospheric pressure air plasma reactor 70 to decompose a small amount of toxic vapor or material including peroxide which can remain inside the chamber 10. By this, additional post-processing device for decomposing the toxic vapor or material is unnecessary.

Generally, in the case of non-thermal atmospheric pressure air plasma, generated plasma free radicals are quickly diluted or destroyed as they are emitted to the open air, which is inappropriate for decontaminating and sterilizing chemical agent or pathogenic biological agent which contaminates objects or gaps which stay away from the exit of plasma. In the present invention, however, free radicals of the generated plasma are not emitted to the open air but entered into the decontamination/sterilization chamber 10 and remained inside the chamber for a predetermined time so that the free radicals such as active species and ozone can interact with the objects of decontamination/sterilization for a long time, thereby enhancing the efficiency of decontamination/sterilization. Also, in the case of evaporized peroxide vapor, as the vapor passes through non-thermal atmospheric pressure air plasma reactor 70, a portion of the vapor generates by plasma discharge strong oxidation free radical such as hydroxyl radical or peroxy radical. Also, ozone or one-valence oxygen which is generated at the air plasma reactor 70 has oxidation activity in itself, and generates more active hydroxy or perhydroxy radicals through interaction with peroxide vapor, thereby increasing the concentration of the free radicals inside the decontamination/sterilization chamber 10 and enhancing the efficiency of decontamination/sterilization.

For the non-thermal atmospheric pressure air plasma reactor 70 used in the present invention as described above, reactor by dielectric barrier discharge (DBD) is appropriate due to low power consumption and small heat generation during being discharged.

In the plasma discharge using dielectric barrier, discharge is generated between two metal electrodes, at least one of the two metal electrodes being coated with dielectric material or catalytic material is filled between the two electrodes.

Figure 3:
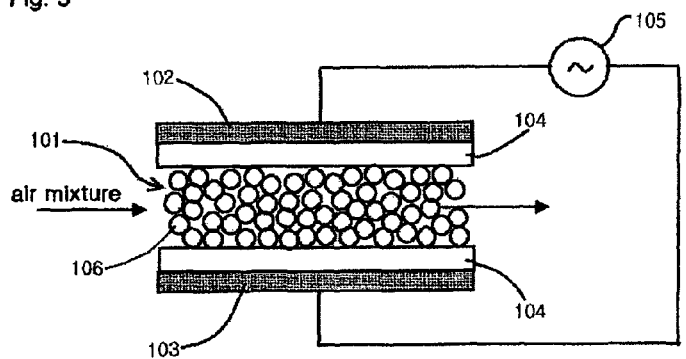
FIG. 3 is a cross section of the plasma/catalyst hybrid reactor in which absorption agent and catalyst are filled in the discharge space of the flat-type dielectric barrier discharge plasma reactor.
Figure 4:
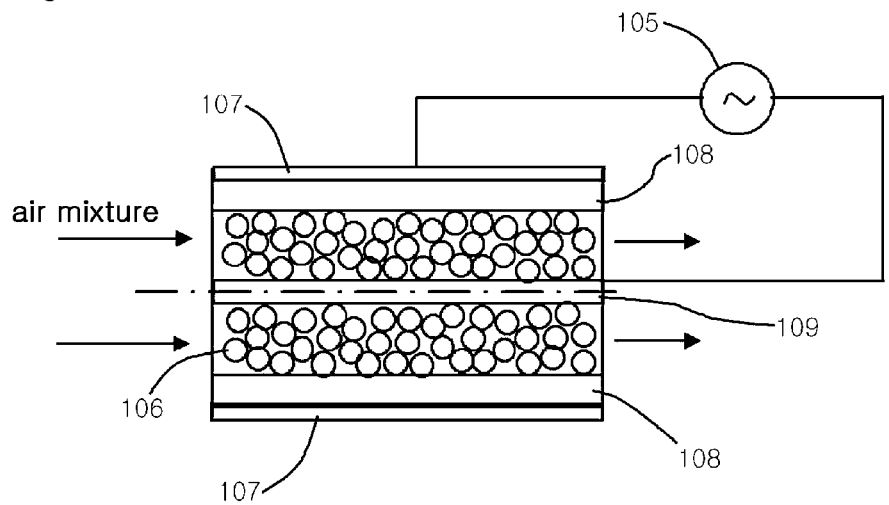
FIG. 4 is a cross section of the plasma/catalyst hybrid reactor in which absorption agent and catalyst are filled in the discharge space of the coaxial plasma reactor.
Figure 5:
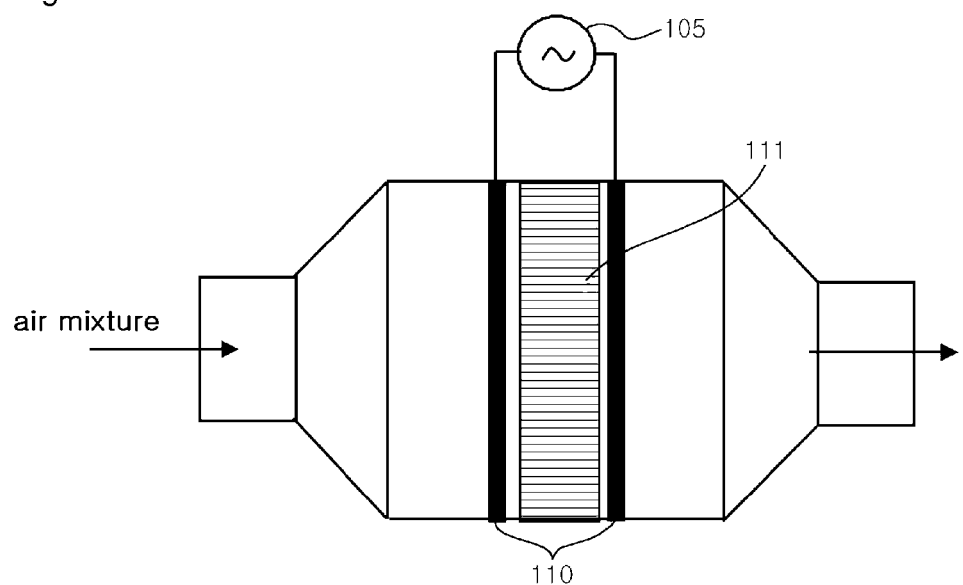
FIG. 5 is a cross section of the ceramic honeycomb plasma reactor.

The electrodes of the plasma reactor, as described above and shown in FIGS. 2 and 3, can be consist of two flat-type electrodes or, as shown in FIG. 4, can be consist of coaxial external electrode and core internal electrode. Also, as shown in FIG. 5, the catalytic material filled between the two electrodes is one-body ceramic honeycomb with catalytic material coated on the surface, or bead-type, pallet-type or granule-type aggregates. The catalytic material coated can be metal oxide with precious metal such as Pt, Pd, Rh or Ru is supported, metal oxide with transition metal oxide such as CrOx or CuOx is supported, molecular sieve such as zeolite 13X, or semiconductor such as $TiO_2$, $ZrO_2$ or $MgO$. When this filling material is filled, micro-discharge can be induced, thereby enhancing energy efficiency and lowering plasma discharge onset voltage.

Figure 2:
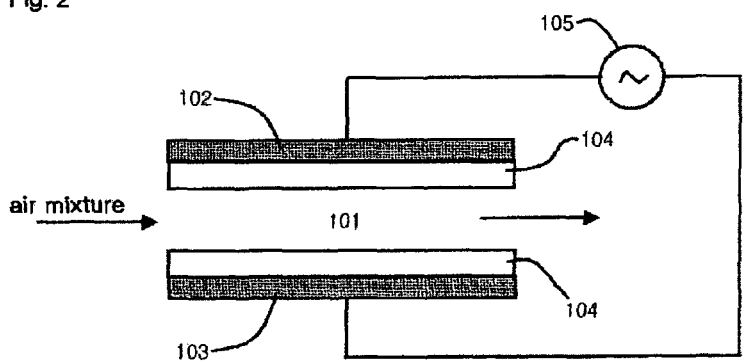
FIG. 2 is a cross section of the flat-type dielectric barrier discharge plasma reactor.

Describing in more detail, FIG. 2 shows representative dielectric barrier discharge plasma reactor, wherein two opposing metal electrodes 102, 103 are connected to alternative power supply 105 and the electrodes are coated or closely contacted with dielectric material 104 to prevent the discharge current from directly flow between the electrodes. The dielectric material is preferably dense ceramic material such as crystal glass or alpha alumina, but any dielectric material can be used as long as the object of the invention can be obtained.

When the voltage supplied from the power supply 105 to the electrodes 102, 103 becomes sufficiently high, discharge occurs at the discharge space 101 between the electrodes, and the voltage necessary for the discharge depends on various factors including the distance between the two electrodes, thickness of the dielectric material and properties of the medium. In the present invention, it is preferable to supply alternative voltage of 5-30 kV with frequency range of 50 Hz-50 kHz, but direct current can be used if necessary. Also, inductance and charging circuit can be installed for impedance matching with the reactor.

FIG. 3 illustrates a reactor with the same reactor as shown in FIG. 2 but filled inside the reactor with filling material 106 of bead or pallet-type made of dielectric material with dielectricity higher than that of air. The filling material has property of adsorbing toxic gas or catalytic property, and can be activated by the dielectric heat generated by the plasma discharge, providing the effect of catalytic interaction as well as a low temperature plasma interaction.

FIG. 4 illustrates a reactor wherein adsorbent or catalyst is filled inside a coaxial (line pipe) plasma reactor, the external tube 108 being made of crystal or alumina material, and metal thin film is coated or closely contacted to the exterior of the tube for use as an electrode 107. Also, metal bar or wire can be used as an internal electrode 109, and plasma discharge occurs in the space between the internal electrode and external tube when power supply 105 is supplied. At this time, proper distance should be maintained between the two electrodes since discharge power increases in accordance with the distance.

FIG. 5 shows another type of plasma reactor for attaining the object of the present invention, which can generate plasma more easily by inserting ceramic honeycomb 111 between the two porous metal electrodes 110 coated with dielectric material, and enables decomposing toxins through plasma reaction and catalytic reaction. Here, direct current or pulse current can be used as well as alternative current. In FIG. 5, the arrangement of the honeycomb micro-channel is in parallel with the flow of air, thereby lowering air resistance and therefore considerably lowering plasma discharge onset voltage due to the honeycomb. The honeycomb can be made of ceramic material such as cordierite, mullite or alumina, and precious metal catalyst or metal oxide catalyst can be coated on the surface of the honeycomb, thereby providing oxidationdecomposition effect by catalyst reaction. Also, when semiconductor material that can provide the function of photocatalyst such as TiO2 is coated on the surface of the honeycomb or when the material is mixed in manufacturing the honeycomb, the effect of photocatalyst can be expected from the UV rays generated by the plasma discharge. In FIG. 5, the electrode 110 can be closely contacted with the honeycomb 111 or has some distance with the honeycomb, but discharge onset voltage becomes high if the distance to the honeycomb is too large or if the thickness of the honeycomb itself is too large. Therefore, the thickness of the honeycomb is preferably not larger than 10 cm, and the distance between the electrode and honeycomb is preferably not larger than 1 cm. For more efficiency of removal, the construction of the honeycomb-electrode as shown in FIG. 5 can be configured more than two inside the housing 12 to increase the staying time of toxic gases.

Meanwhile, at the first fluid supplying line L1 is installed a nitrogen-containing base gas supply 50 which supplies nitrogen-containing base gas into the decontamination/sterilization chamber 10 when necessary in order to control pH of the oxidizing peroxide vapor. The nitrogen-containing base gas supply 50 can be connected to the peroxide vapor supplier, especially to the fluid mixer 60 installed between the vaporizer 40 and the decontamination/sterilization chamber 10, or directly to the decontamination/sterilization chamber 10.

Here, the peroxide is hydrogen peroxide. The concentration of the hydrogen peroxide in aqueous solution state is 20%-70%, or preferably 35% which is commercially available. And, the nitrogen-containing base gas for controlling pH of the oxidizing peroxide vapor is preferably amine, or more preferably ammonia.

In the path between the peroxide aqueous solution supply 30 and the vaporizer 40 is installed a peroxide fluid control valve for controlling the amount of fluid of oxidizing peroxide, and in the path between the nitrogen-containing base gas supply and the mixer is installed a nitrogen-containing base gas fluid control valve for controlling the amount of fluid of the nitrogen-containing base gas.

Also, a dehumidifier is installed on the second fluid supplying line L2, which circulates the carrier gas or the air only for controlling the relative humidity inside the decontamination/sterilization chamber not higher than 40% at room temperature. Here, the method of dehumidification is preferably method using cool coil or peltier method, but not limited to these methods. The system should be dehumidified since, as described below, it is necessary to lower the relative humidity of the air supplied into the decontamination/sterilization chamber when the non-thermal atmospheric pressure air plasma reactor 70 is not operated. Also, it is necessary to remove the water (water vapor) generated from the decomposition of the large portion of the peroxide vapor passing through the non-thermal atmospheric pressure air plasma reactor 70 when the non-thermal atmospheric pressure air plasma reactor 70 is operated.

Also, at the front end of the non-thermal atmospheric pressure air plasma reactor 70 and the front end of the peroxide vapor supplier is installed a blower 100 for blowing air or air mixture.

Also, at the first fluid supplying line L1, heater is installed between the vaporizer 40 and the blower, and at the second fluid supplying line L2, heater is installed at the rear end of the dehumidifier.

Meanwhile, around the inlet 11 of the decontamination/sterilization chamber is installed a temperature gauge. The temperature gauge measures the temperature of the saturated peroxide vapor and air mixture just before they are supplied to the decontamination/sterilization chamber, which is preferably in the range of 55-65° C. The temperature range is controlled by the heater 20, 90 installed at the front end of the vaporizer 40 and at the rear end of the dehumidifier 80 for heating air or air mixture. The purpose is to sufficient amount of peroxide is evaporated and contained in the carrier gas in vapor state so that micro-condensation is easily generated on the surface of the object of decontamination/sterilization by the temperature difference with the object when saturated peroxide vapor is supplied into the decontamination/sterilization chamber. In other words, as saturated peroxide vapor is supplied into the decontamination/sterilization chamber 10, the temperature of the object of decontamination/sterilization is about below 30° C. and the temperature difference makes the peroxide vapor remain on the surface of the object, thereby causing micro-condensation. At this step, the temperature should not be too high since when the temperature of the saturated peroxide vapor exceeds 65° C., especially above 75° C., there is a danger of explosion of peroxide.

Also, around the exit 12 of the decontamination/sterilization chamber is installed a temperature/humidity gauge and a fluid gauge for measuring temperature/humidity and the amount of fluid of the air mixture comprising peroxide vapor, air and water vapor, and also installed is a gas concentration gauge for measuring the concentration of the peroxide vapor in the air mixture. These temperature/humidity gauge, fluid gauge and gas concentration gauge are controlled in connection with the controller. Here, the temperature/humidity gauge measures the air mixture exited through the exit 12 of the decontamination/sterilization chamber 10 for controlling the heater and the dehumidifier so that the inside of the decontamination/sterilization chamber 10 is in the state of predetermined temperature/humidity (temperature: 30° C. or less, relative humidity: 40% or less). Then, the fluid gauge measures the amount of air mixture exited and is necessary for checking the operation of the blower, the amount of fluid measured being depend on the scale of the whole system. Also, gas concentration gauge is necessary for measuring the concentration of the peroxide vapor in the air mixture exited in order to control the supply of the peroxide, and is also necessary for confirming the time of completion of the whole process in the post-processing step which will be described later.

The method for decontaminating and sterilizing chemical and biological agents using the apparatus of the present invention as described above will now be described.

The method for decontaminating and sterilizing chemical and biological agents according to the present invention treats a certain surface contaminated by chemical and biological agent with a mixture of non-thermal atmospheric pressure air plasma and oxidizing peroxide vapor, and comprises the following three steps.

The first step is a stabilization step for attaining appropriate temperature and humidity for the whole system, the second step being decontamination/sterilization step, and the third step post-processing step which decomposes toxins such as peroxide remaining inside the decontamination/sterilization chamber.

In the first step, the object for decontamination/sterilization is placed in the decontamination/sterilization chamber 10, the chamber is closed, and then air which is a carrier gas is circulated by only operating the second fluid supplying line L2. At this step, the relative humidity inside the system is controlled not being higher than 40% at room temperature (20-30° C.) by using a dehumidifier 80 so that both the system and the surface of the object for decontamination/sterilization are in dried state. Here, the non-thermal atmospheric pressure air plasma reactor 70 is not operated. When the temperature and humidity inside the system is sufficiently stabilized, the operation of the second fluid supplying line L2 is stopped and the second step is started.

In the second step, the first fluid supplying line L1 is operated to supply saturated peroxide vapor which is evaporated by the vaporizer 40 into the decontamination/sterilization chamber 10, the temperature of a mixture of air and the saturated peroxide vapor just before entering the decontamination/sterilization chamber 10 is controlled between 55-65° C. In this way, when the saturated peroxide vapor is supplied into the decontamination/sterilization chamber 10, micro-condensation of peroxide vapor is generated on the surface of the object for decontamination/sterilization inside the decontamination/sterilization chamber 10 or on the surface of the decontamination/sterilization chamber 10 due to the temperature difference between the room temperature and inside the decontamination/sterilization chamber, thereby efficiently decontaminating and sterilizing the chemical and biological agents contaminating the surface of the object. The peroxide vapor is continuously supplied through the first fluid supplying line L1 for a predetermined time so that micro-condensation of peroxide vapor is sufficiently generated on every surface inside the decontamination/sterilization chamber 10, the concentration of the water vapor of the system being controlled under dew point during the step. After sufficient micro-condensation of peroxide vapor is generated, the supply of the peroxide vapor is stopped and the carrier gas or air is circulated through the first fluid supplying line L1. The sufficiency of micro-condensation of peroxide vapor is determined by naked eye or by using devices that measures refractivity of light.

In order to enhance the effect of decontamination/sterilization, the second fluid supplying line L2 is operated along with the first fluid supplying line L1 so that non-thermal atmospheric pressure air plasma reactor 70 is operated to convert part of a mixture of peroxide vapor or water (water vapor), which is exited through the exit 12 of the decontamination/sterilization chamber 10 to free radicals such as ozone ($O3$) or one-valence oxygen ($1O2$), and active species such as hydroxyl radical or peroxy radical, which is to be supplied and circulated along with peroxide vapor into the decontamination/sterilization chamber 10. At this step, the fluid velocity of the second fluid supplying line L2 is controlled not to exceed 20% of the fluid velocity of the first fluid supplying line L1 so that peroxide in the recycled fluid is not excessively destroyed. The reactive species such as ozone or radicals which are supplied into the decontamination/sterilization chamber 10 by themselves have the effect of destroying chemical and biological agents, and generating other free radicals through the interaction with the peroxide, thereby providing the effect of accelerating decontamination/sterilization. Therefore, synergistic effect can be expected since decontamination/sterilization effects due to the micro-condensation of the saturated hydrogen peroxide vapor and decontamination/sterilization effects due to the free radicals resulting from air plasma discharge can occur simultaneously.

When the target toxins is chemical agent, especially, in order to enhance the effect of decontamination, pH of the oxidizing peroxide vapor can be controlled when necessary by supplying nitrogen-containing base compound such as amine, specifically ammonia inside the decontamination/sterilization chamber 10 along with peroxide vapor and air plasma. This is especially useful for decontaminating soman (GD) gas, a nervous gas, and the concentration of the nitrogen-containing base gas is preferably controlled in the range of 1-100 ppm(w).

After sufficiently carrying out decontamination/sterilization of chemical or biological agents, the operation of the first fluid supplying line L1 is stopped, and the second fluid supplying line L2 is operated again, starting the third step.

In the third step, peroxide vapor or other toxins that can remain in the circulating air mixture is destroyed to non-toxins by operating air plasma reactor 70. The peroxide, hydrogen peroxide for example, is decomposed to non-toxic water and oxygen by catalytic reaction with the catalytic material filled in the air plasma reactor 70 due to the heat and UV ray generated by the operation of the air plasma reactor 70, and the water is exited through the dehumidifier, and when hydrogen peroxide is sufficiently destroyed (for example, when the concentration of the hydrogen peroxide vapor exited from the decontamination/sterilization chamber is under 1 ppm) the operation of the air plasma reactor 70 is stopped and the post-processing process is completed.

As described above, The present invention, by using air instead of high cost inert gas such as argon as a carrier gas in atmospheric pressure and low temperature plasma discharge, provides high practicability, and decontamination/sterilization of high precision electronic devices, communication devices, computers or inside of vehicles and air planes in efficient and quick way, which has been impossible in the prior art decontamination method for chemical and biological agent in aqueous solution state. Also post-processing is safely completed by recycling air plasma reactor without using separate post-processing equipments.

The present invention has been described through preferable examples. The examples, however, should not be regarded to limit the invention, and as is obvious to those skilled in the art, can be variously modified within the scope of the present invention. The invention should be interpreted by the claims attached and all the technical ideas which are equivalent with the present invention are deemed to be within the scope of the present invention.

DESCRIPTION OF NUMERALS IN THE DRAWING

10: decontamination/sterilization chamber
20, 90: heater
30: peroxide aqueous solution supply
40: vaporizer
50: nitrogen-containing basic gas supply
60: fluid mixer
70: non-thermal atmospheric pressure air plasma reactor
80: dehumidifier
100: blower
101: discharge space
102, 103, 107, 109, 110: electrode
104: dielectric material
105: power supply
106: filling material
108: tube
111: honeycomb

The invention claimed is:

1. Apparatus for decontaminating and sterilizing chemical and biological agents, which comprises:
a decontamination and sterilization chamber which contains object for decontaminating and sterilizing, and decontaminates and sterilizes chemical and biological agent on the surface of the object;
a first fluid supplying line and a second fluid supplying line, which are installed in the form of closed circuit between the inlet and outlet of the decontamination and sterilization chamber so that fluid can be circulated;
a peroxide vapor supplier which is installed on the first fluid supplying line to supply first fluid, which is oxidizing peroxide vapor, into the decontamination and sterilization chamber through the first fluid supplying line using air as carrier gas;
a non-thermal atmospheric pressure air plasma reactor which is installed on the second fluid supplying line and generates air plasma containing plasma free radical and active species by plasmarizing a portion of mixture of gases comprising peroxide vapor, water vapor and air exited through the exit of the decontamination/sterilization chamber so that the air plasma, as a second fluid, is supplied to the decontamination and sterilization chamber through the rear end of the peroxide vapor supplier; and
a blower which is installed on the front of the non-thermal atmospheric pressure air plasma reactor and on the front of the peroxide vapor supplier in order to blow air or air mixture.

2. The apparatus as set forth in claim 1, wherein the second fluid supplying line is branched from the first fluid supplying line on the exit side of the decontamination/sterilization chamber, and installed connected to the rear end of the supplier.

3. The apparatus as set forth in claim 1, wherein a nitrogen-containing base gas supply is installed inside the decontamination/sterilization chamber to supply nitrogen-containing base gas for controlling pH of the oxidizing peroxide vapor.

4. The apparatus as set forth in claim 3, wherein the air mixture contains a small amount of nitrogen-containing base gas.

5. The apparatus as set forth in claim 4, wherein the nitrogen-containing base gas supply is connected to the fluid mixer installed between the peroxide vapor supplier and the decontamination/sterilization chamber, or directly connected to the decontamination/sterilization chamber.

6. The apparatus as set forth in claim 5, wherein the nitrogen-containing base gas is ammonia.

7. The apparatus as set forth in claim 1, wherein the peroxide vapor supplier includes a peroxide aqueous solution supply that supplies oxidizing peroxide aqueous solution and a vaporizer which is connected to the peroxide aqueous solution supply in order to heat and evaporate the oxidizing peroxide aqueous solution.

8. The apparatus as set forth in claim 1, wherein a dehumidifier is installed on the second fluid supplying line which controls the relative humidity inside the decontamination/sterilization chamber not higher than 40% by circulating a carrier gas only.

9. The apparatus as set forth in claim 1, wherein the non-thermal atmospheric pressure air plasma reactor includes two electrodes that cause dielectric barrier discharge, at least one of which is coated with dielectric material or filled with adsorbent or catalytic material between the electrodes.

10. The apparatus as set forth in claim 9, wherein the non-thermal atmospheric pressure air plasma reactor comprises two flat-type electrodes.

11. The apparatus as set forth in claim 9, wherein the non-thermal atmospheric pressure air plasma reactor comprises an external coaxial electrode and core-type internal electrode.

12. The apparatus as set forth in claim 9, wherein the catalytic material filled between the two electrodes is one-body ceramic honeycomb coated with catalytic material, or one selected from the group consisting of bead, pallet or granule-type aggregates.

13. The apparatus as set forth in claim 1, wherein the chemical and biological agent includes one selected from the group consisting of organic phosphorus based compound that can be used for warfare chemical gas or agricultural agent, sulphur or nitrogen-containing compound, cyan based compound, chloride or fluoride-containing compound, and pathogenic bacteria, virus and toxins that can be used as a biological weapon.

14. The apparatus as set forth in claim 1, wherein the peroxide is hydrogen peroxide.

15. A method for decontaminating and sterilizing chemical and biological agents, which comprises:
a stabilization step in which the object for decontamination/sterilization contaminated by chemical and biological agent is placed in the decontamination/sterilization chamber, the chamber is closed, and controlling relative humidity inside the decontamination/sterilization chamber not higher than 40% at room temperature by circulating air which is a carrier gas;
a decontamination/sterilization step in which, after the stabilization step is completed, micro-condensation of peroxide vapor is generated on the surface of the object for decontamination/sterilization and inside the decontamination/sterilization chamber by evaporating peroxide aqueous solution and supplying and circulating the vapor inside the decontamination/sterilization chamber; and a post-processing step in which, after the decontamination/sterilization step is completed, a portion of the air mixture consisting of peroxide vapor, water vapor and air exited from the exit of the decontamination/sterilization chamber is plasmarized through the non-thermal atmospheric pressure air plasma reactor, then additional decontamination of the surface of the objects and inside surface of the decontamination/sterilization chamber is carried out by using air plasma comprising plasma free radicals and active species and toxic material including peroxide remaining in the decontamination/sterilization chamber is decomposed into harmless material.

16. The method as set forth in claim 15, wherein the decontamination/sterilization step comprises a step of supplying, along with the peroxide vapor, plasma free radical and active species generated by simultaneously operating the non-thermal atmospheric pressure air plasma reactor to the decontamination/sterilization chamber.

17. The method as set forth in claim 15, wherein the decontamination/sterilization step comprises a step of controlling pH of the peroxide vapor supplied to the decontamination/sterilization chamber by supplying nitrogen-containing base gas to the decontamination/sterilization chamber.

18. The method as set forth in claim 17, wherein the nitrogen-containing base gas is ammonia.

19. The method as set forth in claim 17, wherein the nitrogen-containing base gas is ammonia.

20. The method as set forth in claim 15, wherein the peroxide vapor and the air mixture are controlled in the temperature range of 55-65° C. before the peroxide vapor and the air mixture are supplied to the decontamination/sterilization chamber.

21. The method as set forth in claim 20, wherein the peroxide is hydrogen peroxide.

22. The method as set forth in claim 15, wherein the peroxide is hydrogen peroxide.

23. The method as set forth in claim 15, wherein the chemical and biological agent includes one selected from the group consisting of organic phosphorus based compound that can be used for warfare chemical gas or agricultural agent, sulphur or nitrogen-containing compound, cyan based compound, chloride or fluoride-containing compound, and pathogenic bacteria, virus and toxins that can be used as a biological weapon.

24. The method as set forth in claim 15, wherein the chemical and biological agent includes one selected from the group consisting of organic phosphorus based compound that can be used for warfare chemical gas or agricultural agent, sulphur or nitrogen-containing compound, cyan based compound, chloride or fluoride-containing compound, and pathogenic bacteria, virus and toxins that can be used as a biological weapon.

* * * * *